(12) United States Patent
Agouridas et al.

(10) Patent No.: US 6,455,505 B2
(45) Date of Patent: *Sep. 24, 2002

(54) DERIVATIVES . . . USE AS MEDICAMENTS

(75) Inventors: Constantin Agouridas, Nogent sur Marne; Alexis Denis; Claude Fromentin, both of Paris, all of (FR)

(73) Assignee: Hoechst Marion Roussel (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/433,146

(22) Filed: Nov. 3, 1999

(30) Foreign Application Priority Data

Nov. 1, 1998 (FR) .............................. 98 14145

(51) Int. Cl.[7] .......................... A61K 31/70; C07H 17/08
(52) U.S. Cl. ............................. 514/29; 536/7.2; 536/7.4
(58) Field of Search ...................... 536/7.2, 7.5; 579/29

(56) References Cited

U.S. PATENT DOCUMENTS

| | | | | |
|---|---|---|---|---|
| 5,543,400 A | * | 8/1996 | Agouridas et al. | 571/29 |
| 5,635,485 A | * | 6/1997 | Agourida et al. | 574/29 |
| 5,747,467 A | * | 5/1998 | Agouridas et al. | 571/59 |
| 5,786,339 A | * | 7/1998 | Agouridas et al. | 536/7.9 |

FOREIGN PATENT DOCUMENTS

| | | |
|---|---|---|
| FR | 2669337 | 5/1992 |
| FR | 2742757 | 6/1997 |
| WO | 9809978 | 3/1998 |
| WO | 9840392 | 9/1998 |

OTHER PUBLICATIONS

XP004138245, A. Denis et al, Bioorganic. . . Letters 8 (1998), pp. 2427–2432 Synthesis. . . Oxime.
XP004138245 Bioorganic & Medicinal Chemistry Letters 8 (1998), pp. 2427–2432 Synthesis. . . Oxime.

* cited by examiner

*Primary Examiner*—Elli Peselev
(74) *Attorney, Agent, or Firm*—Bierman, Muserlian and Lucas

(57) ABSTRACT

A subject of the invention is, as new chemical products, the compounds of formula (I)

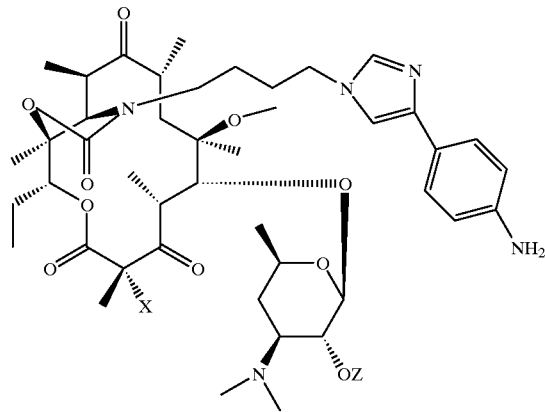

in which X represents a hydrogen atom or a halogen atom and Z represents a hydrogen atom or the remainder of an acid as well as their addition salts with acids. The compounds of formula (I) have antibiotic properties.

10 Claims, No Drawings

DERIVATIVES ... USE AS MEDICAMENTS

The present invention relates to new derivatives of eryrthromycin, their preparation process and their use as medicaments.

A subject of the invention is, as new chemical products, the compounds of formula (I)

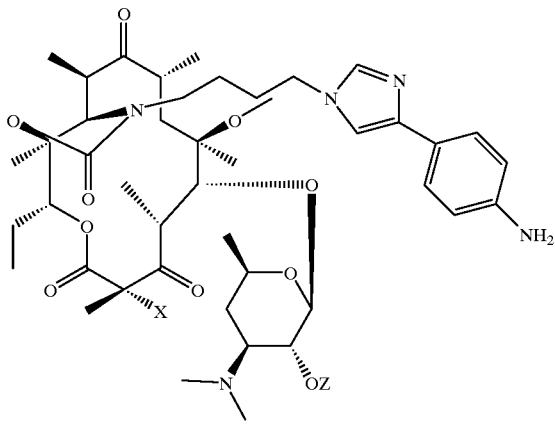

in which X represents a hydrogen atom or a halogen atom and Z represents a hydrogen atom or the remainder of an acid as well as their addition salts with acids.

Among the addition salts with acids, the salts formed with acetic, propionic, trifluoroacetic, maleic, tartaric, methanesulphonic, benzenesulphonic, p-toluenesulphonic acids and particularly stearic, ethylsuccinic or laurylsulphonic acids, can be mentioned.

The halogen atom is for example a chlorine or fluorine atom and preferably a fluorine atom.

A more particular subject of the invention is the compounds of formula (I) in which Z represents a hydrogen atom.

A more particular subject of the invention is the compounds, the preparation of which is given hereafter in the experimental part.

The products of general formula (I) have a very good antibiotic activity on gram $\oplus$ bacteria such as staphylococci, streptococci, pneumococci.

The products are particularly active on strains which are resistant to erythromycin such as for example *Streptococcus pyogenes* and *Streptococcus pneumoniae* and *S. aureus* which have an inducible resistance to erythromycin.

The compounds of the invention can therefore be used as medicaments in the treatment of germ-sensitive infections and in particular, in that of staphylococcia such as staphylococcal septicaemias, malignant staphylococcia of the face or skin, pyodermitis, septic or suppurating wounds, boils, anthrax, phlegmons, erysipelas and acne, staphylococcia such as primitive or post-influenzal acute angina, bronchopneumonia, pulmonary suppuration, streptococcia such as acute angina, otitis, sinusitis, scarlatina, pneumococcia such as pneumonia, bronchitis, and diphtheria. The products of the present invention are also active against infections caused by germs such as *Haemophilus influenzae*.

Therefore a subject of the invention is the compounds of formula (I) as medicaments.

More especially a subject of the invention is, as medicaments, the compounds indicated above as preferred compounds.

A subject of the invention is also the pharmaceutical compositions containing at least one of the medicaments defined above, as active ingredient.

These compositions can be administered by buccal, rectal, parenteral route, or by local route as a topical application on the skin and mucous membranes, but the preferred administration route is the buccal or injectable route. They can be solids or liquids and be presented in the pharmaceutical forms commonly used in human medicine, such as for example, plain or sugar-coated tablets, gelatin capsules, granules, suppositories, injectable preparations, ointments, creams, gels; they are prepared according to the usual methods. The active ingredient or ingredients can be incorporated with the excipients usually used in these pharmaceutical compositions such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

These compositions can also be presented in the form of a powder intended to be dissolved extemporaneously in an appropriate vehicle, for example, apyrogenic sterile water.

The dose administered is variable according to the affection treated, the patient in question, the administration route and the product considered. It can be, for example, comprised between 50 mg and 3000 mg per day by oral or injectable route for an adult for the preferred products.

A subject of the invention is also a preparation process characterized in that a compound of formula (II):

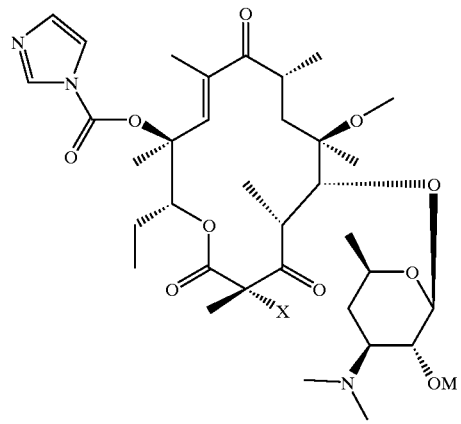

in which X retains its previous meaning and OM represents the remainder of an acyl radical is subjected to the action of a compound of formula (III)

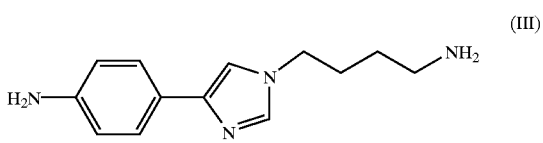

in order to obtain the corresponding compound of formula (IA) then if desired the compound of formula (IA) is subjected to the action of an agent of the hydroxyl function in position 2' and/or if appropriate, to the action of an acid in order to form the salt.

the reaction of the compound of formula (II) with the compound of formula (III) takes place in a solvent such as for example acetonitrile, dimethylformamide or also tetrahydrofuran, dimethoxy ethane or dimethylsulphoxide, the hydrolysis of the ester function in position 2' is carried out using methanol or aqueous hydrochloric acid, the salification is carried out using acids according to standard processes.

The compounds of formula (II) in which X represents a hydrogen atom, which are used as starting products are described and claimed in European Patent Application 0 596 802.

The compounds of formula (II) which are used as starting products in which X represents a fluorine atom can be prepared as indicated hereafter in the experimental part.

Compound III is a new product and is itself a subject of the present invention.

EXAMPLE 1

11,12-dideoxy-3-de[(2,6-dideoxy-3-C-methyl-3-0-methyl-alpha-L-ribohexopyranosyl)oxy]-6-0-methyl-3-oxo-12,11-[oxycarbonyl-[[4-[4-(4-aminophenyl)-1H-imidazol-1-yl]butyl]imino]]-eryrthromycin A mixture containing 0.690 g of the product of Preparation 1, 14 ml of THF, 14 ml of isopropanol, 1.41 g of 2'-acetate and 12-[(1H-imidazol-1-yl)carboxylate]of 10,11-didehydro-11-deoxy-3-de [(2,6-dideoxy-3-C-methyl-3-0-methyl-alpha-L-ribohexopyranosyl)oxy]-6-0-methyl-3-oxo-erythromycin and 60 μl of DBU is agitated for 48 hours at ambient temperature. The reaction medium is poured into water, extracted with ethyl acetate, washed with water, dried, filtered and concentrated. 1.54 g of product is obtained which is taken up in 15 ml of methanol with 0.015 ml of DBU added to it. The methanol is driven off under reduced pressure and 1.44 g of product is obtained which is chromatographed on silica eluting with a methylene chloride, methanol, ammonium hydroxide mixture 93-7-0.4. 0.84 g of product is obtained which is taken up in ethyl acetate, water and ammonium hydroxide, followed by extracting, drying, filtering and concentrating. 0.8 g of product is obtained which is chromatographed on silica eluting with an ethyl acetate methanol triethylamine mixture. 0.4 g of product is obtained which is crystallized from ether, separated and dried. 0.270 g of sought product is obtained. M.p.=188~190° C.

Mass spectrum MH$^+$=826$^+$

NMR CDCl$_3$ ppm

| Number | &'H | Number | &'H |
|---|---|---|---|
| 1 | | 1' | 4.28 (d) |
| 2 | 3.86 q | 2' | 3.18 (m) |
| 3 | | 3' | 2.45 (m) |
| 4 | 3.07 (m) | 4' | 1.24–1.68 (m) |
| 5 | 4.24 (d) | 5' | 3.53 (m) |
| 6 | | 5' Me | 1.25 (d) |
| 7 | 1.60–1.82 (m) | N (Me)$_2$ | 2.26 (s) |
| 8 | 2.60 masked | NCH$_2$ | 3.64–3.72 (m) |
| 9 | | CH$_2$ | 1.65 (m) |
| 10 | 3.13 (m) | CH$_2$ | 1.85 (m) |
| 11 | 3.57 (s) | CH$_2$N | 3.95 (t) |
| 12 | | N imidazole | 7.10–7.45 |
| 13 | 4.94 (dd) | 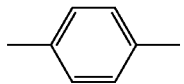 | 6.70 (d) 7.56 (d) |
| 14 | 1.54–1.92 (m) | NH$_2$ | 13.53 |
| 15 | 0.84 (t) | | |
| 2Me | 1.38 (d) | | |
| 4Me | 1.30 (d) | | |

| Number | &'H | Number | &'H |
|---|---|---|---|
| 6Me | 1.34,or,1.48 (s) | | |
| 8Me | 1.17 (d) | | |
| 10Me | 1.00 (d) | | |
| 12Me | 1.34 or 1.48 (s) | | |
| 60Me | 2.63 (s) | | |

Preparation 1

4-(4-aminophenyl)-1H-imidazole-1-butanamine

Stage A: 4-(4-nitrophenyl)-1H-imidazole 9.7 g of 2-bromo-1-(4-nitrophenyl)-ethanone and 30 ml of formamide are agitated for 1 hour at 180° C. The reaction medium is cooled down and poured into water. The pH of the reaction medium is adjusted to 1 using a solution of hydrochloric acid and extracted with ethyl acetate. The aqueous phase has concentrated ammonium hydroxide added to it, followed by saturating with sodium chloride and extracting with ethyl acetate. The organic phase is dried, filtered and concentrated under reduced pressure. 7.09 g of product is obtained which is impasted in the ethyl ether, separated and dried. 4.74 g of product is obtained melting at 216–218° C.

Stage B: 2-[4-[4-(4-nitrophenyl)-1H-imidazole-1-yl]butyl]-1H-isoindole-1,3(2H)-dione.

A solution containing 4.7 g of the product of the preceding stage and 15 ml of DMF is introduced into a mixture containing 1.44 g of sodium hydride and 12.5 ml of DMF. A solution containing 7.05 g of N-(4-bromobutyl) phthalimide and 17.5 ml of DMF is added. Agitation is carried out for 3 hours at ambient temperature. The reaction medium is poured into a mixture of water and ice, extracted with ethyl acetate, washed with water, dried, filtered and concentrated. 6.77 g of product is obtained which is chromatographed on silica eluting with an ethyl acetate triethylamine mixture 95-5. 2.29 g of product is obtained melting at 170~172° C.

Stage C: 2-[4-[4-(4-aminophenyl)-1H-imidazole-1-yl]butyl]-1H-isoindole-1,3(2H)-dione.

A mixture of 2 g of product of the preceding stage, 41 ml of a methanol, methylene chloride mixture.(20.5 ml–20.5 ml) and 200 mg of 10% palladium on carbon is agitated at ambient temperature under hydrogen pressure for 3 hours. The reaction medium is filtered, washed with a methylene chloride methanol mixture 50-50 and concentrated under reduced pressure. 1.6 g of product is obtained which is used as it is in the following stage.

Stage D: 4-(4-aminophenyl)-1H imidazole-1-butanamine

A mixture containing 1.6 g of product of the preceding stage, 1.1 ml of hydrazine hydrate and 35.5 cm$^3$ of absolute ethanol is taken to reflux for 24 hours. The reaction medium is cooled down to ambient temperature, filtered, rinsed with ethanol, concentrated under reduced pressure, taken up in methylene chloride, filtered and concentrated. 0.71 g of sought product is obtained.

EXAMPLE 2

2-fluoro-11,12-dideoxy-3-de[(2,6-dideoxy-3-C-methyl-3-0-methyl-alpha-L-ribohexopyranosyl)oxy]-6-0-methyl-3-oxo-12,11-[oxycarbonyl[[4-[4-(4-aminophenyl)-1H-imidazol-1-yl]butyl]imino]]-eryrthromycin By operating as previously starting with the product of Preparation 2, the sought product is obtained. TLC: ethyl acetate/triethylamine 90-10. Rf 0.20

Preparation 2

2'-acetoxy 2 α-fluoro of 12-(oxycarbonylimidazol)11-deoxy 10,11-didehydro 3- de [(2,6-dideoxy 3-C-methyl 3-0-methyl α-L-ribohexopyranosyl)oxy] 6-0-methyl 3-oxo erythromycin.

Stage A: 11l-deoxy 10,11-didehydro 3-de[(2,6-dideoxy 3-0-methyl α-L-ribohexopyranosyl) oxy]6-0-methyl 3-oxo eryrthromycin.

A mixture of 8.722 g of 2'-acetate of 11-deoxy 10,11-didehydro 3-de[(2,6-dideoxy 3-0-methyl α L-ribohexopyranosyl)oxy]6-0-methyl 3-oxo eryrthromycin (EP 596802) and 350 ml of anhydrous methanol is agitated for 44 hours. 8.794 g of sought product is obtained.

Stage B: 2'-trimethylsilyloxy of 11-deoxy 10,11-didehydro 3-de [(2,6-dideoxy 3-0-methyl α-L-ribohexopyranosyl)oxy] 6-0-methyl 3-oxo eryrthromycin.

A mixture containing 3.08 g of the product of the preceding stage, 340 mg of imidazole, 32 ml of THF anhydre and 1.06 ml of hexamethyl-disilylazane is agitated at ambient temperature for 4 days, followed by evaporating to dryness, taking up in a mixture of 60 ml of methylene chloride and 60 ml of 0.5M sodium acid phosphate. The reaction mixture is maintained under agitation for 15 minutes, decanted, extracted with methylene chloride, dried and evaporated to dryness. 3.345 g of sought product is obtained.

Stage C: 2'-trimethylsilyloxy 2α-fluoro of 11-deoxy 10,11-didehydro 3-de [(2,6-dideoxy 3-0-methyl α-L-ribohexo-pyranosyl)oxy] 6-0-methyl 3-oxo eryrthromycin.

1.24 ml of a solution of potassium terbutylate in THF 0.97M is added at −12° C. under an argon atmosphere to a solution containing 668 mg of 2'-trimethylsilyloxy of 11-deoxy 10,11-didehydro 3-de [(2,6-dideoxy 3-0-methyl α-L-ribohexopyranosyl)oxy]6-0-methyl 3-oxo eryrthromycin and 6.7 ml of anhydrous THF. The reaction medium is agitated for 5 minutes and 378 mg of N-fluoro dibenzene-sulphonimide is added. Agitation is carried out for 10 minutes at −12° C. and the reaction medium is left for 1 hour 30 minutes to return to ambient temperature. Isolation and purification operations are carried out and 695 mg of sought product is obtained.

Stage D: 2α-fluoro of 11-deoxy 10,11-didehydro 3- de [(2,6-dideoxy 3-0-methyl 3-0-methyl α-L-ribohexopyranosyl)oxy] 6-0-methyl 3-oxo eryrthromycin A mixture of 5.476 g of the product of the preceding stage, 50 ml of THF and 11.2 ml of 1M tetrabutylammonium fluoride in THF is agitated for 3 hours 30 minutes. The solvent is evaporated off and 37 ml of ethyl acetate, 37 ml of water and 7.5 ml of 20% ammonium hydroxide are added. Agitation is carried out for 10 minutes, followed by decanting, extracting with ethyl acetate, drying, filtering and concentrating the filtrate to dryness. The product obtained is chromatographed on silica eluting with an ammoniated $CH_2Cl_2$-MeOH mixture 99-1, then 98-2, 97-3, 96-4, 95-5. 2.452 g of sought product is obtained.

Stage E: 2'-acetoxy 2α-fluoro of 11-deoxy 10,11-didehydro 3-de [(2,6-dideoxy 3-0-methyl α-L-ribohexopyranosyl)oxy] 6-0-methyl 3-oxo eryrthromycin 1.02 g of the product of Stage D, 10 ml of methylene chloride and 241 µl of acetic anhydride are maintained under agitation for 3 hours. After evaporation is carried out, 10 ml of water and 10 ml of ethyl acetate are added. The reaction medium is left under agitation for 1 hour at ambient temperature, decanted, dried and evaporated. 1.01 g of sought product is obtained.

Stage F: 2'-acetoxy 2α-fluoro of 12-(oxycarbonyllimidazol) 11-deoxy 10,11-didehydro 3- de [(2,6-dideoxy 3-C-methyl-3-0-methyl α-L-ribohexopyranosyl) oxy] 6-0-methyl 3-oxo eryrthromycin 0.388 g of carbonyldiimidazole and 24 µl of DBU is added at 0° C. to a solution containing 1.01 g of the product of the preceding stage and 10 ml of anhydrous THF. The THF is evaporated off and 10 ml of water and 10 ml of ethyl acetate are added. The reaction mixture is maintained under agitation for 10 minutes, extracted, dried and evaporated. 0.902 g of crude sought product is obtained which is chromatographed eluting with an ethyl acetate-triethylamine mixture 96-4. 0.573 g of sought product is obtained.

EXAMPLES OF PHARMACEUTICAL COMPOSITIONS

Tablets were prepared containing:

| | |
|---|---|
| Product of Example 1 | 150 mg |
| Excipient s.q.f. | 1 g |

Detail of excipient: starch, talc, magnesium stearate

| | |
|---|---|
| Product of Example 2 | 150 mg |
| Excipient s.q.f. | 1 g |

Detail of excipient: starch, talc, magnesium stearate Injectable solutions were also prepared from salified compounds.

PHARMACOLOGICAL STUDY OF THE PRODUCTS OF THE INVENTION

A—Method of Dilutions in Liquid Medium

A series of tubes were prepared in which the same quantity of nutritive sterile medium is distributed. Increasing quantities of the product to be studied are distributed into each tube, then each tube is sown with a bacterial strain. After incubation for 24 hours in a heating chamber at 37° C., the growth inhibition is evaluated by transillumination, which allows the minimal inhibitory concentrations to be determined, expressed in micrograms/cm$^3$. The following results were obtained

| | EX. 1 | EX. 2 |
|---|---|---|
| *Streptococcus pyogenes* | 2.5 | 0.3 |
| *Streptococcus pneumoniae* | 1.2 | 0.150 |

What is claimed is:

1. A compound selected from the group consisting of a compound of the formula

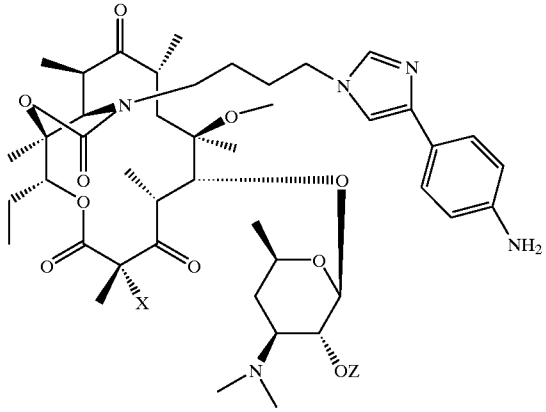

wherein X is hydrogen or halogen, Z is hydrogen or acyl of an acid and its non-toxic, pharmaceutically acceptable acid addition salts.

2. A compound of claim 1 which is 11,12-dideoxy-3-de [(2,6-dideoxy-3-C-methyl-3-0-methyl-alpha-L-ribohexopyranosyl)oxy] 6-0-methyl 3-oxo 12,11-[oxycarbonyl[[4-[4-(4-aminophenyl)-1H-imidazol-1-yl]-butyl]imino]]-erythromycin.

3. A compound of claim 1 which is 2-fluoro-11,12-dideoxy-3-de [(2,6-dideoxy-3-C-methyl-3-0-methyl-alpha-L-ribohexopyranosyl)oxy] 6-0-methyl 3-oxo 12,11-[oxycarbonyl[[4-[4-(4-aminophenyl)-1H-imidazol-1-yl]-butyl]imino]]-erythromycin.

4. A compound of claim 1 wherein X is fluorine.

5. A compound of claim 1 wherein Z is hydrogen.

6. A process for the preparation of a compound of claim 1 comprising reacting a compound of the formula

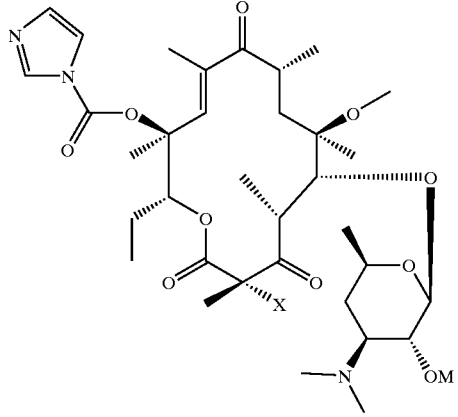

wherein X is hydrogen or halogen and M is an acyl with a compound of the formula

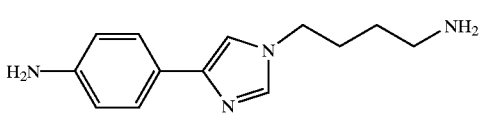

to obtain a compound of formula I wherein Z is acyl and optionally subjecting the latter to hydrolysis to obtain the compounds of formula I wherein Z is hydrogen.

7. An antibacterial composition comprising a bactericidally effective amount of a compound of claim 1 and an inert pharmaceutical carrier.

8. A method of combatting bacterial infections in warm-blooded animals comprising administering to warm-blooded animals a bactericidally effective amount of a compound of claim 1.

9. A method of combatting bacterial infections in warm-blooded animals comprising administering to warm-blooded animals a bactericidally effective amount of a compound of claim 2.

10. A method of combatting bacterial infections in warm-blooded animals comprising administering to warm-blooded animals a bactericidally effective amount of a compound of claim 3.

* * * * *